United States Patent
Feng et al.

(10) Patent No.: US 12,391,998 B2
(45) Date of Patent: Aug. 19, 2025

(54) COMPOSITION AND KIT FOR DETECTING MYCOPLASMA

(71) Applicants: JIANGSU ACADEMY OF AGRICULTURAL SCIENCES, Nanjing (CN); GUOTAI (TAIZHOU) CENTER OF TECHNOLOGY INNOVATION FOR VETERINARY BIOLOGICALS, TAIZHOU, Taizhou (CN)

(72) Inventors: Zhixin Feng, Nanjing (CN); Yanfei Yu, Nanjing (CN); Jia Wang, Nanjing (CN); Yanna Wei, Nanjing (CN); Guoqing Shao, Nanjing (CN); Yuzi Wu, Nanjing (CN); Maojun Liu, Nanjing (CN); Qiyan Xiong, Nanjing (CN); Li Wang, Nanjing (CN); Beibei Liu, Nanjing (CN)

(73) Assignees: JIANGSU ACADEMY OF AGRICULTURAL SCIENCES, Nanjing (CN); GUOTAI (TAIZHOU) CENTER OF TECHNOLOGY INNOVATION FOR VETERINARY BIOLOGICALS, TAIZHOU, Taizhou (CN)

( * ) Notice: Subject to any disclaimer, the term of this patent is extended or adjusted under 35 U.S.C. 154(b) by 0 days.

(21) Appl. No.: 18/911,297

(22) Filed: Oct. 10, 2024

(65) Prior Publication Data
US 2025/0051860 A1    Feb. 13, 2025

Related U.S. Application Data

(63) Continuation of application No. PCT/CN2023/109885, filed on Sep. 6, 2023.

(30) Foreign Application Priority Data

Jun. 16, 2023    (CN) .......................... 202310719274.5

(51) Int. Cl.
C12Q 1/68    (2018.01)
C12Q 1/689    (2018.01)

(52) U.S. Cl.
CPC ....... *C12Q 1/689* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 10,640,834 B2 * | 5/2020 | Shimizu | ................. | C12Q 1/689 |
| 2003/0050470 A1 * | 3/2003 | An | ......................... | C07H 21/00 |
| | | | | 435/6.14 |
| 2004/0023207 A1 * | 2/2004 | Polansky | ............. | A61K 48/005 |
| | | | | 435/456 |
| 2007/0117120 A1 | 5/2007 | Anderson et al. | | |
| 2017/0240959 A1 * | 8/2017 | Shimizu | ................... | C12Q 1/68 |

FOREIGN PATENT DOCUMENTS

| | | | |
|---|---|---|---|
| CN | 105420379 A | 3/2016 | |
| CN | 110343777 A | 10/2019 | |
| CN | 110894534 A | 3/2020 | |
| JP | 2004305207 A | 11/2004 | |
| KR | 2013128334 A | * 11/2013 | ............. C12N 15/11 |

OTHER PUBLICATIONS

Dreolini et al., 2020. A rapid and sensitive nucleic acid amplification technique for mycoplasma screening of cell therapy products. Molecular Therapy—Methods & Clinical Development, 17, pp. 393-399. (Year: 2020).*
Fourour et al., 2018. A new multiplex real-time TaqMan® PCR for quantification of *Mycoplasma hyopneumoniae*, M. hyorhinis and M. flocculare. Journal of applied microbiology, 125(2), pp. 345-355 (Year: 2018).*
English Translation of KR2013-0128334A, pub Nov. 11, 26, 2013. (Year: 2013).*
Gadberry MD, Malcomber ST, Doust AN, Kellogg EA. Primaclade—a flexible tool to find conserved PCR primers across multiple species. Bioinformatics. Apr. 1, 2005; 21(7):1263-4. Epub Nov. 11, 2004. (Year: 2004).*
Genbank Accession No. AF443616—Mycoplasma hominis DNA, complete cds, submitted Jul. 26, 2006, retrieved on Jan. 25, 2025 from http://www.ncbi.nlm.nih.gov/nuccore/AF443616). (Year: 2006).*
Lee, J.I. and Kim, I.S., 2014. TaqMan probe real-time PCR for quantitative detection of mycoplasma during manufacture of biologics. KSBB Journal, 29(5), pp. 361-371. (Year: 2014).*
Molla Kazemiha et al., 2016. Real-time PCR assay is superior to other methods for the detection of mycoplasma contamination in the cell lines of the National Cell Bank of Iran. Cytotechnology, 68, pp. 1063-1080. (Year: 2016).*
Salling et al., 2016. Multi-primer qPCR assay capable of highly efficient and specific detection of the vast majority of all known Mycoplasma. Biologicals, 44(3), pp. 129-138. (Year: 2016).*
SantaLucia Jr., John. Physical principles and visual-OMP software for optimal PCR design. PCR Primer Design. Humana Press, 2007: pp. 3-33. (Year: 2007).*

(Continued)

*Primary Examiner* — Gary Benzion
*Assistant Examiner* — Olayinka A Oyeyemi
(74) *Attorney, Agent, or Firm* — Bayramoglu Law Offices LLC (57) ABSTRACT

A composition and a kit for detecting *mycoplasma* are provided. The composition for detecting *mycoplasma* is an aqueous solution including a primer M-F, a primer M-R, and a probe M-P. A sequence of the M-F is shown in SEQ ID NO: 1. A sequence of the M-R is shown in SEQ ID NO: 2. A nucleotide sequence of the probe M-P is shown in SEQ ID NO: 3, and includes a fluorophore FAM linked at a 5' terminus and a quencher BHQ1 linked at a 3' terminus. The composition exhibits high sensitivity, strong specificity, and a wide detection range when used in the detection of *mycoplasma*.

10 Claims, 6 Drawing Sheets

Specification includes a Sequence Listing.

(56) References Cited

OTHER PUBLICATIONS

Siegl et al., May 19, 2023. A PCR protocol to establish standards for routine mycoplasma testing that by design detects over ninety percent of all known mycoplasma species. Iscience, 26(5) 10672413, pp. 1-13. (Year: 2023).*

Stormer et al., 2009. Broad-range real-time PCR assay for the rapid identification of cell-line contaminants and clinically important mollicute species. International journal of medical microbiology, 299(4), pp. 291-300. (Year: 2009).*

Sugita et al., 2021. Detection of mycoplasma contamination in transplanted retinal cells by rapid and sensitive polymerase chain reaction Test. International Journal of Molecular Sciences, 22, 12555, p. 1-13 (Year: 2021).*

Sung et al., 2020. A highly sensitive internally-controlled real-time PCR assay for mycoplasma detection in cell cultures. Biologicals, 64, pp. 58-72. (Year: 2020).*

Svenstrup et al., 2005. Development of a quantitative real-time PCR assay for detection of Mycoplasma genitalium. Journal of Clinical Microbiology, 43(7), pp. 3121-3128. (Year: 2005).*

Wambulawaye, P.P., Dec. 2022. Development of a multiplex real-time PCR to distinguish between Mycoplasma species found in South African poultry (Master's thesis, University of Pretoria (South Africa)) pp. 1-149 (Year: 2022).*

Boonyayatra et al., 2012: A PCR assay and PCR-restriction fragment length polymorphism combination identifying the primary Mycoplasma species causing mastitis J Dairy Sci 95: 196-205. (Year: 2012).*

Liang Zhe, et al., Effect of the Endogenous Spinal Cord Substances on the Survival of the Neurons of Spinal Cord in Vitro, 1996, pp. 134-139, vol. 18 No. 3.

Huo Xin-Yang, et al., Establishment and Application of Multiplex Quantitative PCR Method for Detection of Mycoplasma, Progress in Modern Biomedicine, 2020, pp. 1259-1262, vol. 20 No. 7.

M. E. Pollock, et al., Isolation and Elimination of Pleuropneumonia-Like Organisms From Mammalian Cell Cultures, PPLO Elimination from Cell Cultures, 1960, pp. 10-15.

Lucili.E B. Robinson, et al., Contamination of Human Cell Cultures by Pleuropneumonialike Organisms, Science, 1956, pp. 1147-1148, vol. 124.

Commission Of Chinese Veterinary Pharmacopoeia, Veterinary Pharmacopoeia of the People's Republic of China, 2020, pp. 3301-3302, ISBN: 9787109275867.

Liu Jiang, et al., Detection of Mycoplasma Contamination in Cell Cultures by Polymerase Chain Reaction, Journal of Cell Biology, pp. 134-139, vol. 18 No. 3.

* cited by examiner

FIG. 5B

COMPOSITION AND KIT FOR DETECTING MYCOPLASMA

CROSS REFERENCE TO THE RELATED APPLICATIONS

This application is a continuation application of International Application No. PCT/CN2023/109885, filed on Sep. 6, 2023, which is based upon and claims priority to Chinese Patent Application No. 202310719274.5, filed on Jun. 16, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBHS014-PKG_Sequence_Listing_20241023.xml, created on Oct. 23, 2024, and is 8,906 bytes in size.

TECHNICAL FIELD

The present disclosure belongs to the field of biotechnologies, and specifically relates to a composition and kit for detecting mycoplasma.

BACKGROUND

Mycoplasma contamination is one of the major challenges for cell culture. In 1956, researchers at Johns Hopkins reported the mycoplasma contamination of HeLa cells used in the laboratory, and it was the first time mycoplasma was detected in a cell culture. Mycoplasma-contaminated cells can undergo weakened metabolism and slowed proliferation. However, due to the non-lethality of mycoplasma contamination for cells, mycoplasma often coexists with cells for a long time and generally does not cause a significant morphological change in cells. At an early stage of mycoplasma contamination, the medium does not become turbid, which makes it difficult to determine whether the cell culture undergoes mycoplasma contamination with naked eyes. However, mycoplasma-contaminated cells may undergo a series of biological changes, such as a change in composition of the cell membrane, chromosomal abnormalities, a change in the enzyme system, and a change in the viral load, which can mislead scientific research tremendously and seriously interfere with experimental results.

The main sources of mycoplasma as a contaminant for cell culture are animal serum, trypsin, and aerosols. Acholeplasma laidlawii (A. laidlawii) (one of the most common contaminants) can also come from soil and other inanimate sources. Since the trypsin commonly on the market is acquired from commercially available porcine pancreases, Mycoplasma hyorhinis (M. hyorhinis) can also enter the cell culture through this reagent. As early as 1960, Pollock et al. found that 57% of 166 mammalian cell lines and sublines were contaminated with mycoplasma. Studies have shown that, in terms of the in vitro growth of mammalian cells, a mycoplasma-contaminated cell culture undergoes slowed growth and a shortened logarithmic growth phase.

The "Veterinary Pharmacopoeia of the People's Republic of China" stipulates the following two methods for detecting mycoplasma: the cultivation method and the DNA fluorescent staining method. However, when the conventional cultivation method is used to detect mycoplasma, there are disadvantages such as a heavy workload and a long cycle time. Some mycoplasma individuals with strict nutritional requirements may be missed, and there may be false positives of contamination due to the large time span during cultivation. The DNA fluorescent staining method has high sensitivity, but the result is not easy to determine and is easily affected by the subjective determination of the detector. The DNA fluorescent staining method takes about 1 week, which is slightly shorter than the time required by the cultivation method. There are many other limiting factors for the application of the DNA fluorescent staining method in scientific research. There is a lack of mycoplasma detection methods with high sensitivity, strong specificity, and a wide detection range in the art.

SUMMARY

An objective of the present disclosure is to provide a composition for detecting mycoplasma, with high sensitivity, strong specificity, and wide detection range.

The objective of the present disclosure is allowed through the following technical solutions:

The present disclosure provides a composition for detecting mycoplasma, where the composition is an aqueous solution including a primer M-F, a primer M-R, and a probe M-P; a sequence of the M-F is shown in SEQ ID NO: 1; a sequence of the M-R is shown in SEQ ID NO: 2; and a nucleotide sequence of the probe M-P is shown in SEQ ID NO: 3, and includes a fluorophore carboxyfluorescein (FAM) linked at a 5' terminus and a quencher black hole quencher 1 (BHQ1) linked at a 3' terminus.

In the present disclosure, the primer M-F, the primer M-R, and the probe M-P are in a molar concentration ratio of 1:(0.8-1.2): (0.8-1.2).

The present disclosure also provides a kit for detecting mycoplasma, including the composition.

In the present disclosure, the primer M-F, the primer M-R, and the probe M-P in the kit are in a molar concentration ratio of 1:(0.8-1.2): (0.8-1.2).

In the present disclosure, the kit further includes a positive plasmid, and the positive plasmid is obtained by inserting a fragment with a sequence shown in SEQ ID NO: 4 into a pUC57 plasmid vector.

The present disclosure also provides a method for detecting mycoplasma using the composition for a non-diagnostic purpose, including the following steps:
(1) extracting DNA from a sample;
(2) with the DNA of the sample as a template, conducting quantitative polymerase chain reaction (qPCR) detection using the primer M-F, the primer M-R, and the probe M-P; and
(3) when a cycle threshold (Ct) value of the qPCR detection for the DNA of the sample is smaller than 38 and there is a typical S-type amplification curve, determining as positive, indicating that there is mycoplasma in the sample; and when the Ct value of the qPCR detection for the DNA of the sample is larger than or equal to 38 or there is no Ct value or there is no typical S-type amplification curve, determining as negative, indicating that there is no mycoplasma in the sample.

In the present disclosure, a reaction system for the qPCR detection includes: 12.5 µL of a fluorescent polymerase chain reaction (PCR) solution, 1 µL of the DNA of the sample, 3 µL of the composition, and 8.5 µL of double distilled water (ddH$_2$O).

In the present disclosure, a procedure for the qPCR is as follows: 95° C. for 3 min; 95° C. for 15 sec, and 60° C. for 30 sec, with 40 amplification cycles in total.

The composition of the present disclosure exhibits high sensitivity, strong specificity, and a wide detection range when used in the detection of mycoplasma. A total of 106 random cell samples from different laboratories in different regions are collected for testing. Positive samples detected by the composition of the present disclosure have a coincidence rate of 100% with position samples detected by the cultivation method, and a detection time is significantly shortened.

BRIEF DESCRIPTION OF THE DRAWINGS

FIGS. 1A-1B show detection results of the qPCR method in Example 1, where

FIGS. 3A-3C show detection results of mycoplasma by a commercial qPCR kit, where

DETAILED DESCRIPTION OF THE EMBODIMENTS

Example 1 Composition, Kit, and Method for Detecting Mycoplasma

1. Composition for Detecting Mycoplasma

In order to find a highly-sensitive and universal qPCR method for detecting mycoplasma, the applicants conducted genome-wide alignment analysis for 143 mycoplasma sequences published in an NCBI database, and designed dozens of pairs of primers and probes. It was found that only one pair of primers (M-F and M-R) and a probe M-P could detect the tested 15 mycoplasma species with high sensitivity.

A sequence (SEQ ID NO: 1) of the M-F was as follows: 5'-ATCCATCCCCACGTTCTCGT-3'. A sequence (SEQ ID NO: 2) of the M-R was as follows: 5'-TGCGGTGAATACGTTCTCGGG-3'. A nucleotide sequence (SEQ ID NO: 3) of the probe M-P was as follows: 5'-ACGGGCGGTGTGTACA-3', with a fluorophore FAM (carboxyfluorescein) linked at a 5' terminus and a quencher BHQ1 (succinimide ester) linked at a 3' terminus.

The composition for detecting mycoplasma was an aqueous solution including 10 μM of the M-F, 10 μM of the M-R, and 10 μM of the probe M-P.

2. qPCR Method for Detecting Mycoplasma

The qPCR method for detecting mycoplasma included the following steps:

(1) DNA was extracted from a sample.

(2) qPCR detection:

With the DNA of the sample as a template, qPCR was conducted. A total reaction system for the qPCR was of 25 μL, including: 12.5 μL of a fluorescent PCR solution (Vazyme, Item No. Q112-AA), 1 μL of the DNA of the sample, 3 μL of the composition for detecting mycoplasma, and 8.5 μL of ddH$_2$O. The reaction system was specifically shown in Table 1. A PCR tube with the total reaction system for qPCR was placed in a detection hole of an ABI fluorescence PCR instrument. An FAM channel was selected for detection (quencher: BHQ-1), a reaction system was set to 25 μL, and cycle parameters were set as follows: 95° C. for 3 min, 95° C. for 15 sec, and 60° C. for 30 sec, with 40 amplification cycles in total. At the end of annealing in each cycle, an FAM fluorescence signal was acquired.

In addition, a negative control and a positive control were set. The negative control and the positive control were the same as the qPCR detection method except that the DNA of the sample was replaced with ddH$_2$O in the negative control and the DNA of the sample was replaced with a positive plasmid DNA in the positive control. The positive plasmid DNA used in the positive control was a positive plasmid obtained by ligating a gene fragment Spiroplasma (with a sequence shown in SEQ ID NO: 4) from S. citri to a pUC57 plasmid vector through two enzyme cleavage sites of BamHI and XhoI. The positive plasmid was chemically transformed into a competent Escherichia coli (E. coli) strain XL10 for proliferation.

TABLE 1

| qPCR system | |
|---|---|
| Component | System (μL) |
| Fluorescent PCR solution | 12.5 |
| Composition for detecting mycoplasma | 3 |
| Sterile nuclease-free water (ddH$_2$O) | 8.5 |
| DNA of the sample (10 ng/μL) | 1 |
| Total | 25 |

(3) Result Determination

When a Ct value of the qPCR detection for the DNA of the sample was smaller than 38 and there was a typical S-type amplification curve, it was determined as positive, indicating that there was mycoplasma in the sample. When the Ct value of the qPCR detection for the DNA of the sample was larger than or equal to 38 or there was no Ct value or there was no typical S-type amplification curve, it was determined as negative, indicating that there was no mycoplasma in the sample.

Example 2 Specificity and Sensitivity of qPCR

1. Specificity (1) 15 mycoplasma species, various bacteria, viruses, and different cells each were detected by the qPCR method in Example 1. The 15 mycoplasma species were A. laidlawii, M. fermentans, M. hyorhinis, M. orale, M. arginini, Mp, MG, MS, S. citri, Mhs, Mh, M. pirum, Mf, Mb, and MO, respectively. The various bacteria, viral nucleic acids, and different cells included *Salmonella pullorum* (*S. pullorum*), *E. coli*, *Staphylococcus aureus* (*S. aureus*), *Pseudomonas fragi* (*P. fragi*), Yeast, porcine circovirus type 2 (PCV-2), pseudorabies virus (PRV), porcine reproductive and respiratory syndrome virus (PRRSV), African green monkey kidney cells (Vero), porcine kidney cells (PK-15), canine kidney cells (MDCK), human laryngeal epidermoid carcinoma cells (Hep-2), mouse mononuclear macrophage leukemia cells (RAW264.7), or the like.

Figure 1A:
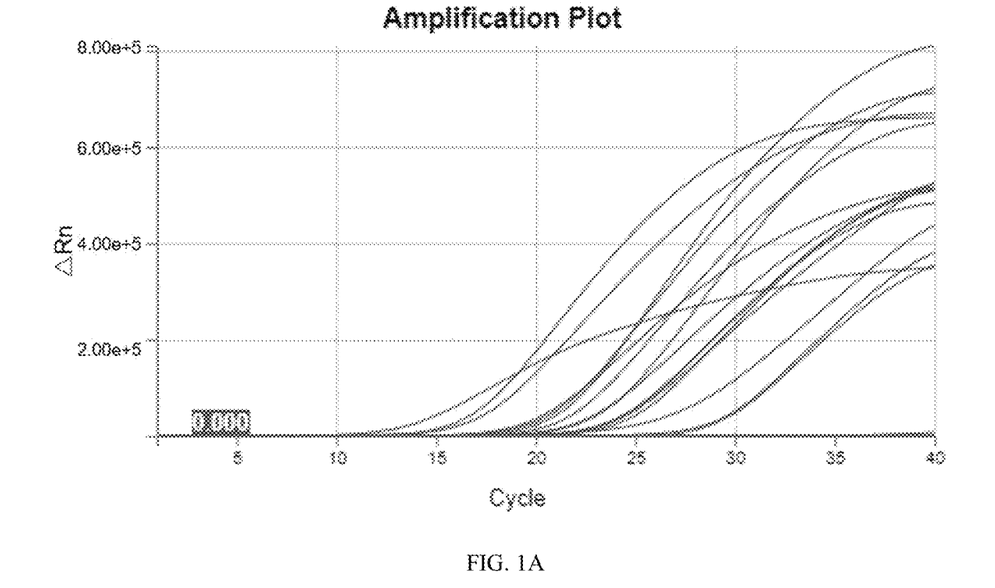
FIG. 1A shows qPCR detection results of 15 mycoplasma species and FIG. 1B shows qPCR detection results of cells, bacteria, and viruses.
Figure 1B:
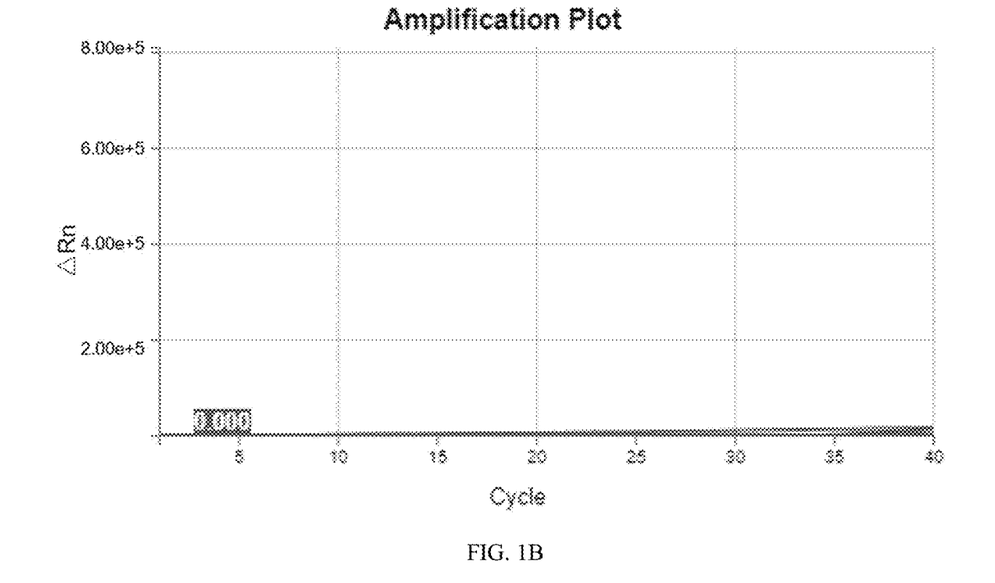

When the qPCR method in Example 1 was used to detect the above-mentioned common cells, viruses, and bacteria, no peak appeared. When the qPCR method in Example 1 was used to detect DNA of the above 15 *mycoplasma* species, a Ct value was smaller than 38 (Table 2) and there was a typical S-type amplification curve (FIGS. 1A-1B). The above results show that the qPCR method in Example 1 exhibits excellent broad-spectrum activity and specificity when used in the detection of *mycoplasma*.

TABLE 2

CT values of qPCR detection for the 15 mycoplasma species

| No. | Sample name | CT |
|---|---|---|
| 1 | Neg | Undet |
| 2 | *M. orale* | 21.753 |
| 3 | MS | 11.681 |
| 4 | Mf | 27.571 |
| 5 | Mp | 14.406 |
| 6 | Mb | 27.371 |
| 7 | *M. fermentans* | 21.468 |
| 8 | Mh | 19.990 |
| 9 | *A. laidlawii* | 17.394 |
| 10 | MO | 19.585 |
| 11 | Mhs | 14.090 |
| 12 | *M. arginini* | 17.749 |
| 13 | *S. citri* | 19.131 |
| 14 | MG | 22.151 |
| 15 | *M. pirum* | 18.373 |
| 16 | *M. hyorhinis* | 21.559 |
| 17 | Pos | 21.922 |

Notes: In Table 2, Undet indicates that no CT value is detected, Pos indicates a positive control, and Neg indicates a negative control, the same below.

(2) Commercial Nested PCR Method

The above 15 *mycoplasma* samples in (1) of Title 1 of this example were detected by a commercial nested *mycoplasma* detection PCR kit, GMyc-PCR *Mycoplasma* Test Kit (Yeasen BioTechnologies co., Ltd.).

Operation steps: For a first round of PCR, a reaction system was shown in Table 3 and a reaction procedure was shown in Table 4. After the first round of PCR was completed, an amplification product was collected, diluted 1,000-fold, and then used as a template for a second round of PCR. For the second round of PCR, a reaction system was shown in Table 5 and a reaction procedure was the same as the reaction procedure for the first round of PCR.

TABLE 3

System for the first round of PCR

| Reagent | Experimental group | Positive control | Negative control |
|---|---|---|---|
| GMyc-1st PCR Mix | 25 µL | 25 µL | 25 µL |
| Template DNA | 4 µL | 4 µL | |

TABLE 3-continued

System for the first round of PCR

| Reagent | Experimental group | Positive control | Negative control |
|---|---|---|---|
| ddH₂O | 21 µL | 20 µL | 25 µL |
| Positive quality control template | | 1 µL | |
| Total volume | 50 µL | 50 µL | 50 µL |

TABLE 4

Conditions for the first round of PCR

| PCR conditions | Temperature | Time | Number of reaction cycles |
|---|---|---|---|
| Pre-denaturation | 94° C. | 5 min | |
| Denaturation | 94° C. | 30 sec | 30 |
| Annealing | 58° C. | 30 sec | |
| Extension | 72° C. | 30 sec | |
| Re-extension | 72° C. | 7 min | |

TABLE 5

System for the second round of PCR

| Reagent | Experimental group | Positive control | Negative control |
|---|---|---|---|
| GMyc-2nd PCR Mix | 25 µL | 25 µL | 25 µL |
| ddH₂O | 24 µL | 24 µL | 24 µL |
| Product of the first round of amplification that is diluted 1,000-fold | 1 µL | 1 µL | 1 µL |
| Total volume | 50 µL | 50 µL | 50 µL |

Figure 2:
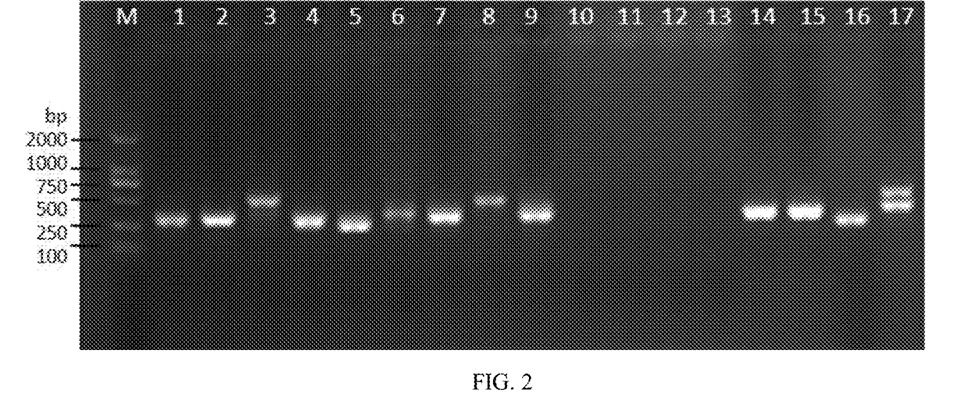
FIG. 2 is an electropherogram illustrating detection results of mycoplasma by a commercial nested mycoplasma detection PCR kit, where M: DL2000 DNA Marker; 1: Mycoplasma gallisepticum (MG); 2: Mycoplasma hyosynoviae (Mhs); 3: Mycoplasma pneumoniae (Mp); 4: Mycoplasma orale (M. orale); 5: M. hyorhinis; 6: A. laidlawii; 7: Mycoplasma fermentans (M. fermentans); 8: Mycoplasma synoviae (MS); 9: Spiroplasma citri (S. citri); 10: Mycoplasma flocculare (Mf); 11: Mycoplasma ovipneumoniae (MO); 12: Mycoplasma hominis (Mh); 13: negative control; 14: positive control; 15: Mycoplasma bovis (Mb); 16: Mycoplasma arginini (M. arginini); and 17: Mycoplasma pirum (M. pirum)

The commercial nested *mycoplasma* detection PCR kit was used to detect the 15 *mycoplasma* species, and results were shown in FIG. 2. Only 12 *mycoplasma* species were detected by the commercial nested *mycoplasma* detection PCR kit. This method required two rounds of PCR and agarose gel electrophoresis, resulting in cumbersome operations. A detection rate of this method was 20% lower than a detection rate of the qPCR method of the present disclosure.

(3) Commercial qPCR Method

The 15 *mycoplasma* samples in (1) of Title 1 of this example were detected by the commercial qPCR kit, MycAway™ *Mycoplasma* Real-time qPCR Detection Kit (Yeasen BioTechnologies co., Ltd.).

Components for the commercial qPCR included 4×qPCR Reaction Buffer, Primer & Probe MIX, positive and negative controls, and sterile nuclease-free water. A qPCR system was shown in Table 6.

FAM was selected as a reporter fluorophore, and MGB was selected as a quenching fluorophore. A reaction system was set to 40 µL. Cycle parameters were set as follows: 95° C. for 5 min, 95° C. for 15 sec, and 62° C. for 30 sec, with 45 amplification cycles in total. At the end of annealing in each cycle, an FAM fluorescence signal was acquired. When Ct was smaller than 40 and there was a clear amplification curve, it was determined as positive. When Ct was greater than or equal to 40 or there was no obvious peak, it was determined as negative.

TABLE 6

| qPCR system | |
|---|---|
| Component | System (μL) |
| 4 × qPCR Reaction Buffer | 10 |
| Primer & Probe MIX | 1 |
| Template (10 ng/μL) | 20 |
| Sterile nuclease-free water | Making up to 40 μL |
| Total | 40 |

Figure 3A:
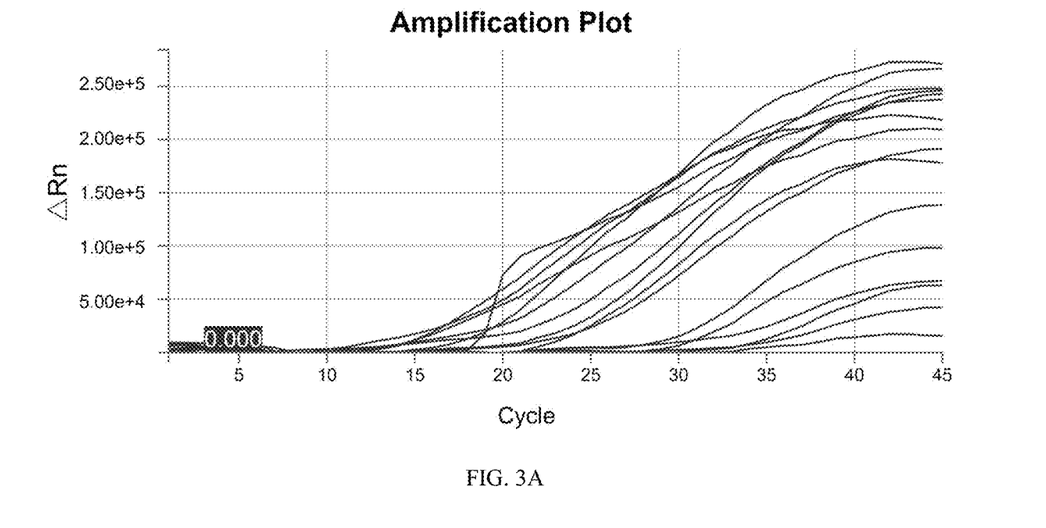
FIG. 3A shows amplification curves of 15 mycoplasma samples.
Figure 3B:
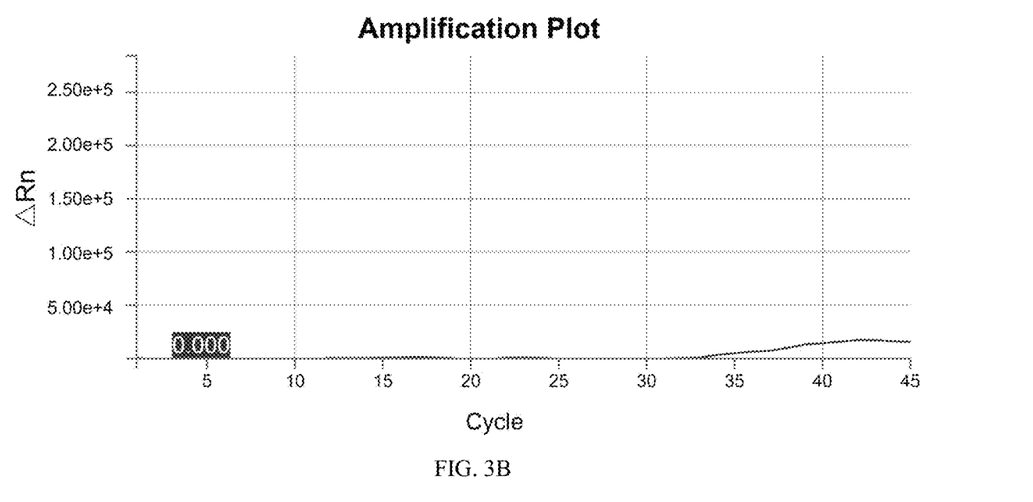
FIG. 3B shows an amplification curve of M. pirum.
Figure 3C:
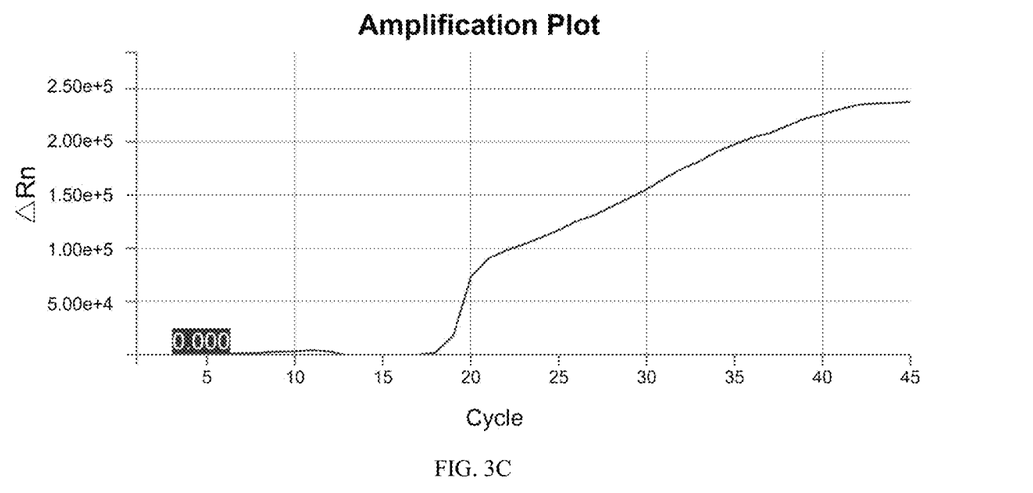
FIG. 3C shows an amplification curve of A. laidlawii.

Detection results of the commercial qPCR kit: CT values are shown in Table 7. It can be seen from FIGS. 3A-3C that S-type amplification curves of *A. laidlawii* and *M. pirum* are atypical and negative. The qPCR method in Example 1 of the present disclosure has significant advantages over the commercial qPCR kit. The commercial qPCR kit requires 20 μL of a template (10 ng/μL), but the method of the present disclosure only requires 1 μL of sample DNA as a template during detection. The commercial qPCR kit requires 45 cycles, but the method of the present disclosure only requires 40 cycles. The method of the present disclosure can amplify a typical S-type amplification curve for all of the 15 *mycoplasma* species, and allows a stronger fluorescence intensity and a smoother curve than the commercial qPCR kit, making it not prone to mis-determination.

TABLE 7

| CT values of 15 mycoplasma species detected by the commercial qPCR kit | | |
|---|---|---|
| No. | Sample | CT |
| 1 | Neg | Undet |
| 2 | *M. orale* | 22.229 |
| 3 | MS | 13.693 |
| 4 | Mf | 22.27 |
| 5 | Mp | 29.855 |
| 6 | Mb | 28.997 |
| 7 | *M. fermentans* | 19.764 |
| 8 | Mh | 21.833 |
| 9 | *A. laidlawii* | 17.9 |
| 10 | MO | 11.621 |
| 11 | Mhs | 13.263 |
| 12 | *M. arginini* | 17.43 |
| 13 | *S. citri* | 11.27 |
| 14 | MG | 33.484 |
| 15 | *M. pirum* | 33.904 |
| 16 | *M. hyorhinis* | 20.428 |
| 17 | Pos | 11.483 |

2. Sensitivity

The *E. coli* carrying the positive plasmid in Example 1 was allowed to proliferate, the positive plasmid was extracted, and a concentration of the positive plasmid was determined by a spectrophotometer. The plasmid was diluted 10-fold serially to produce plasmid concentrations of $10^9$ copies/μL, $10^8$ copies/μL, $10^7$ copies/μL, $10^6$ copies/μL, $10^5$ copies/μL, $10^4$ copies/μL, $10^3$ copies/μL, $10^2$ copies/μL, $10^1$ copies/μL, $10^0$ copies/μL, and $10^{-1}$ copies/μL, respectively. 1 μL of the positive plasmid at each concentration was taken as a template and used for analysis by the qPCR method in Example 1 to investigate the sensitivity of the method. Ten parallel tests were conducted for each concentration.

According to results of the qPCR detection in Example 1 (Table 8): When a concentration of the positive plasmid was $10^{-1}$ copies/μL, a Ct value could not be stably detected in 3 of 10 reactions. When a concentration of the positive plasmid was $10^0$ copies/μL, a Ct value could be stably detected, and the Ct value was smaller than 38. When a concentration of the positive plasmid was $10^{-1}$ copies/μL, a Ct value could not stably appear. Therefore, the sensitivity of the qPCR method was determined to be $10^0$ copies/μL, and a Ct threshold was 38.

TABLE 8

Ct values for the positive plasmid at each concentration detected by the qPCR method

| Sample No. | Plasmid concentration, copies/μL | Ct value | | | | | | | | | |
|---|---|---|---|---|---|---|---|---|---|---|---|
| | | Replicate 1 | Replicate 2 | Replicate 3 | Replicate 4 | Replicate 5 | Replicate 6 | Replicate 7 | Replicate 8 | Replicate 9 | Replicate 10 |
| 1 | $10^9$ | 7.416 | 7.646 | 6.917 | 7.181 | 6.922 | 6.815 | 6.556 | 6.459 | 6.166 | 6.033 |
| 2 | $10^8$ | 10.043 | 10.219 | 10.224 | 10.652 | 10.438 | 10.055 | 10.089 | 10.174 | 10.356 | 9.917 |
| 3 | $10^7$ | 13.589 | 13.893 | 13.928 | 14.406 | 13.567 | 13.699 | 13.913 | 13.839 | 13.750 | 13.469 |
| 4 | $10^6$ | 17.123 | 17.048 | 16.856 | 17.651 | 17.216 | 16.797 | 17.376 | 17.221 | 17.452 | 17.249 |
| 5 | $10^5$ | 20.982 | 20.836 | 21.013 | 21.814 | 20.808 | 21.170 | 20.442 | 20.654 | 20.826 | 20.489 |
| 6 | $10^4$ | 24.245 | 23.758 | 23.759 | 24.866 | 24.428 | 24.446 | 23.974 | 23.801 | 24.213 | 24.229 |
| 7 | $10^3$ | 27.756 | 27.071 | 27.317 | 27.401 | 27.636 | 27.794 | 27.653 | 27.598 | 27.771 | 27.598 |
| 8 | $10^2$ | 31.096 | 30.850 | 31.443 | 31.425 | 31.050 | 30.961 | 30.795 | 31.027 | 30.732 | 31.038 |
| 9 | $10^1$ | 34.070 | 33.923 | 34.237 | 35.380 | 33.048 | 33.617 | 33.814 | 35.409 | 34.259 | 33.539 |
| 10 | $10^0$ | 36.585 | 36.109 | 36.813 | 37.786 | 36.030 | 37.271 | 37.633 | 37.500 | 36.098 | 36.604 |
| 11 | $10^{-1}$ | Undet | 38.289 | 38.254 | 39.541 | 38.572 | 39.894 | Undet | Undet | 38.572 | 38.672 |

When other primers and probes were used to detect *mycoplasma*, such as a primer MP03-F: 5'-GGTCGTC-TACGTCAAAACTTGC-3' (SEQ ID NO: 5), a primer MP03-R: 5'-GCCATTTGGTCCCCGTCAAAG-3' (SEQ ID NO: 6), and a probe MP03-P: FAM-TACCTTGT-TACGACTT-BHQ1 (SEQ ID NO: 7), there was a poor broad-spectrum activity, a typical S-type curve could not be provided for 2 of the 15 tested *mycoplasma* species, and a sensitivity was 102 copies/μL.

Example 3 Detection of *Mycoplasma* Contamination in a Cell Culture by the qPCR Method A total of 106 cell samples from various laboratories were detected by the qPCR method in Example 1, the cultivation method in the 2020 edition of the "*Veterinary Pharmacopoeia of the People's Republic of China*", and the commercial qPCR method for *mycoplasma* to investigate a coincidence rate of the qPCR method in Example 1 with the cultivation method in the 2020 edition of the "*Veterinary Pharmacopoeia of the People's Republic of China*".

1. The qPCR Method in Example 1

A supernatant from each cell sample was taken to prepare a template through boiling. Specific steps were as follows: A supernatant was collected from a cell culture to be tested, added to a centrifuge tube, heated to 100° C. and boiled for 10 min, and cooled. A resulting supernatant was collected and centrifuged for 5 s to 6 s. A resulting supernatant was collected (or subjected to DNA extraction by a kit) as sample DNA for the qPCR detection method.

Figure 4A:
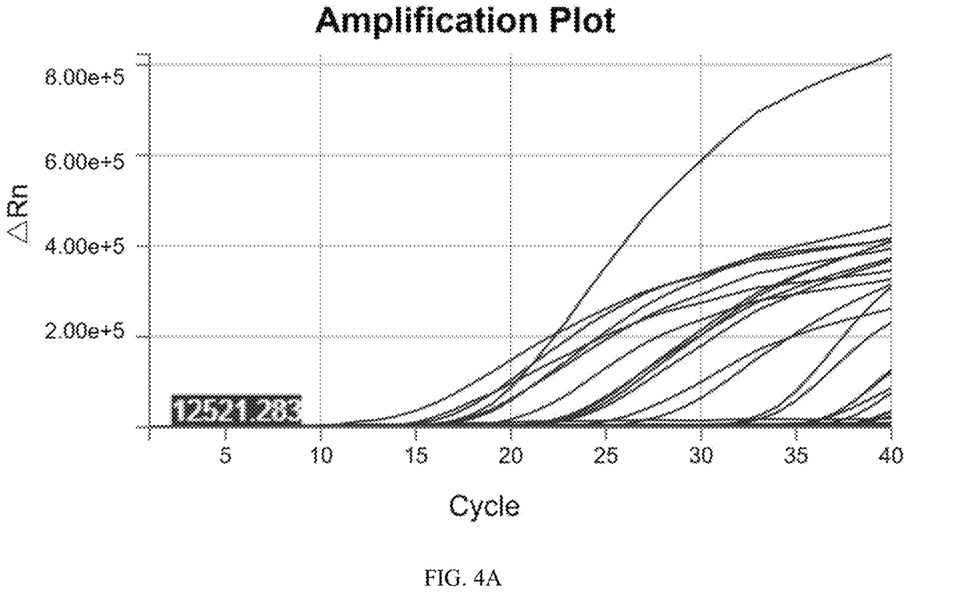
FIGS. 4A-4B show amplification curves of 106 cell samples detected by the qPCR method in Example 1.
Figure 4B:
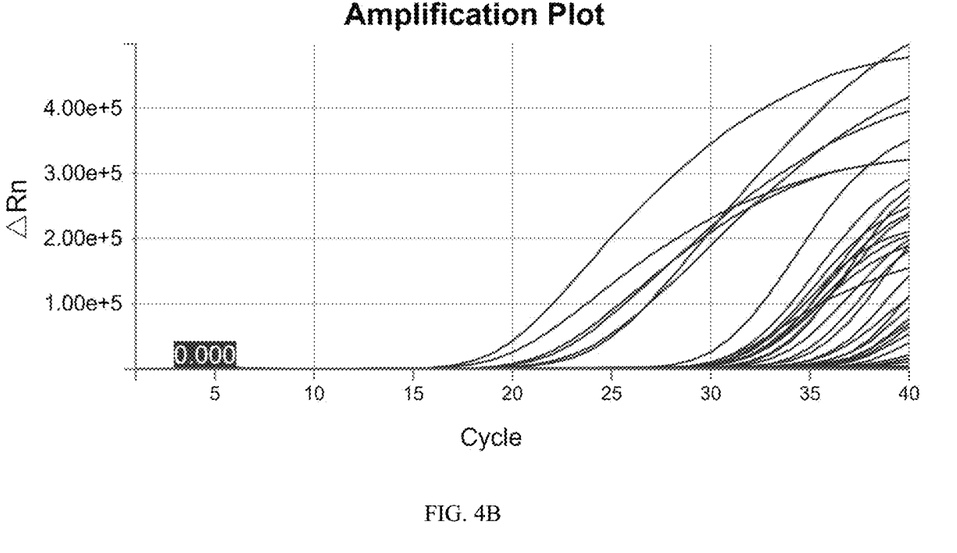

106 cell samples were detected by the qPCR method in Example 1. Results showed that 49 cell samples had a CT value of smaller than 38 (Table 9) and a typical amplification curve, and were positive for *mycoplasma*, as shown in FIGS. 4A-4B. Thus, a positive detection rate was 46.23%.

TABLE 9

CT values of the 106 cell samples detected by the qPCR method in Example 1

| No. | CT |
| --- | --- |
| 1 | 19.488 |
| 2 | Undet |
| 3 | 16.9171 |
| 4 | Undet |
| 5 | 35.608 |
| 6 | 37.0916 |
| 7 | 12.060 |
| 8 | Undet |
| 9 | Undet |
| 10 | Undet |
| 11 | 15.107 |
| 12 | Undet |
| 13 | 32.115 |
| 14 | 17.542 |
| 15 | Undet |
| 16 | Undet |
| 17 | Undet |
| 18 | 32.582 |
| 19 | 15.626 |
| 20 | Undet |
| 21 | 35.800 |
| 22 | 21.760 |
| 23 | 22.583 |
| 24 | 35.458 |
| 25 | Undet |
| 26 | 26.516 |
| 27 | Undet |
| 28 | 37.493 |
| 29 | Undet |
| 30 | 16.7138 |
| 31 | 19.488 |
| 32 | Undet |
| 33 | 16.917 |
| 34 | 34.753 |
| 35 | 35.608 |
| 36 | Undet |
| 37 | Undet |
| 38 | 30.927 |
| 39 | Undet |
| 40 | 30.852 |
| 41 | Undet |
| 42 | 36.566 |
| 43 | Undet |
| 44 | Undet |
| 45 | Undet |
| 46 | 24.987 |
| 47 | Undet |
| 48 | 33.207 |
| 49 | Undet |
| 50 | Undet |
| 51 | 29.805 |
| 52 | Undet |
| 53 | Undet |
| 54 | Undet |
| 55 | Undet |
| 56 | Undet |
| 57 | 21.937 |
| 58 | Undet |
| 59 | 37.089 |
| 60 | 35.917 |
| 61 | Undet |
| 62 | Undet |
| 63 | 36.080 |
| 64 | Undet |
| 65 | 33.638 |
| 66 | Undet |
| 67 | Undet |
| 68 | Undet |
| 69 | 30.617 |
| 70 | Undet |
| 71 | 34.184 |
| 72 | Undet |
| 73 | 32.004 |
| 74 | 30.830 |
| 75 | 20.887 |
| 76 | Undet |
| 77 | Undet |
| 78 | Undet |
| 79 | Undet |
| 80 | 30.945 |
| 81 | 37.245 |
| 82 | 33.399 |
| 83 | Undet |
| 84 | 23.304 |
| 85 | Undet |
| 86 | 32.201 |
| 87 | 25.145 |
| 88 | Undet |
| 89 | Undet |
| 90 | 34.495 |
| 91 | 31.295 |
| 92 | 35.264 |
| 93 | Undet |
| 94 | Undet |
| 95 | Undet |
| 96 | Undet |
| 97 | Undet |
| 98 | 32.169 |
| 99 | Undet |
| 100 | Undet |
| 101 | Undet |

TABLE 9-continued

CT values of the 106 cell samples detected
by the qPCR method in Example 1

| No. | CT |
| --- | --- |
| 102 | 28.480 |
| 103 | Undet |
| 104 | 20.488 |
| 105 | Undet |
| 106 | Undet |
| Positive control | 21.011 |
| Negative control | Undet |

2. Detection of *Mycoplasma* in Cell Samples by the Isolation and Cultivation Method According to the cultivation method in the 2020 edition of the "*Veterinary Pharmacopoeia of the People's Republic of China*", each cell sample was subjected to liquid and solid cultivation. At the end of cultivation, if no *mycoplasma* grew in a medium into which a cell sample was inoculated, the cell sample was qualified, otherwise, the cell sample was unqualified.

If *mycoplasma* grew, a color of a liquid medium would also change (pink or yellow). After aerobic cultivation in a solid medium at 37° C. for 30 d, if *mycoplasma* grew, pinpoint-like colonies could be observed by naked eyes in a medium and fried egg-like colonies could be observed under a microscope. In this experiment, known negative and positive samples were taken as negative and positive controls, respectively.

After about 21 d of cultivation, results showed that liquid media of 24 cell samples turned yellow (a pH decreased), and media of 7 cell samples turned pink (a pH increased). As a result, it was determined that these 31 cell samples were contaminated with *mycoplasma*. Cultures undergoing a color change each were inoculated into a solid medium and cultivated for about 30 d, and then fried egg-like colonies were formed on the solid medium. Thus, a positive detection rate was 29.25%.

3. Detection of *Mycoplasma* in Cell Samples by the Commercial qPCR Kit

Each cell sample was detected with the commercial qPCR kit, MycAway™ *Mycoplasma* Real-time qPCR Detection Kit (Yeasen BioTechnologies co., Ltd.). A specific method was implemented according to instructions.

Figure 5A:
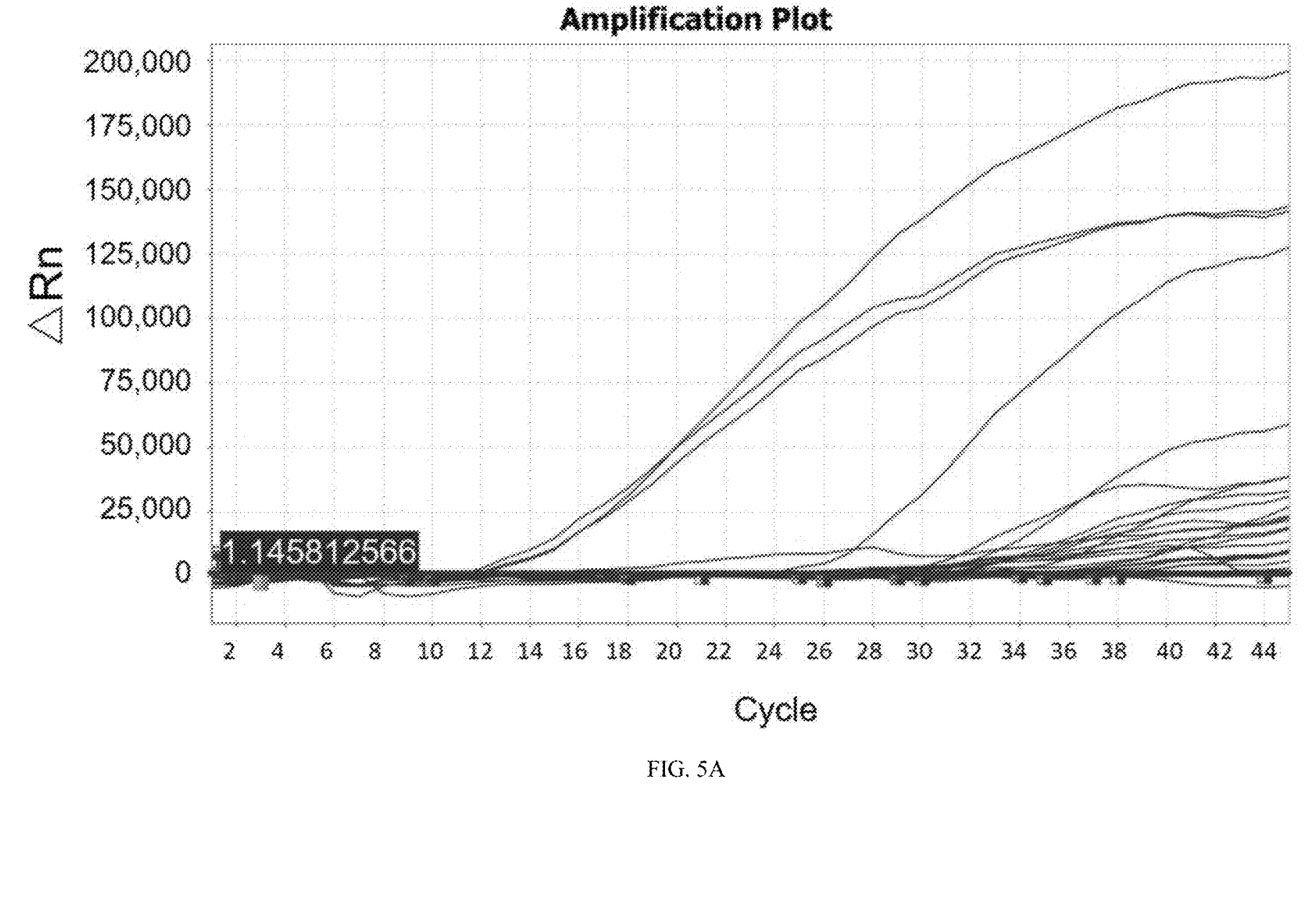
FIGS. 5A-5B show amplification curves of 106 cell samples detected by a commercial qPCR kit.
Figure 5B:
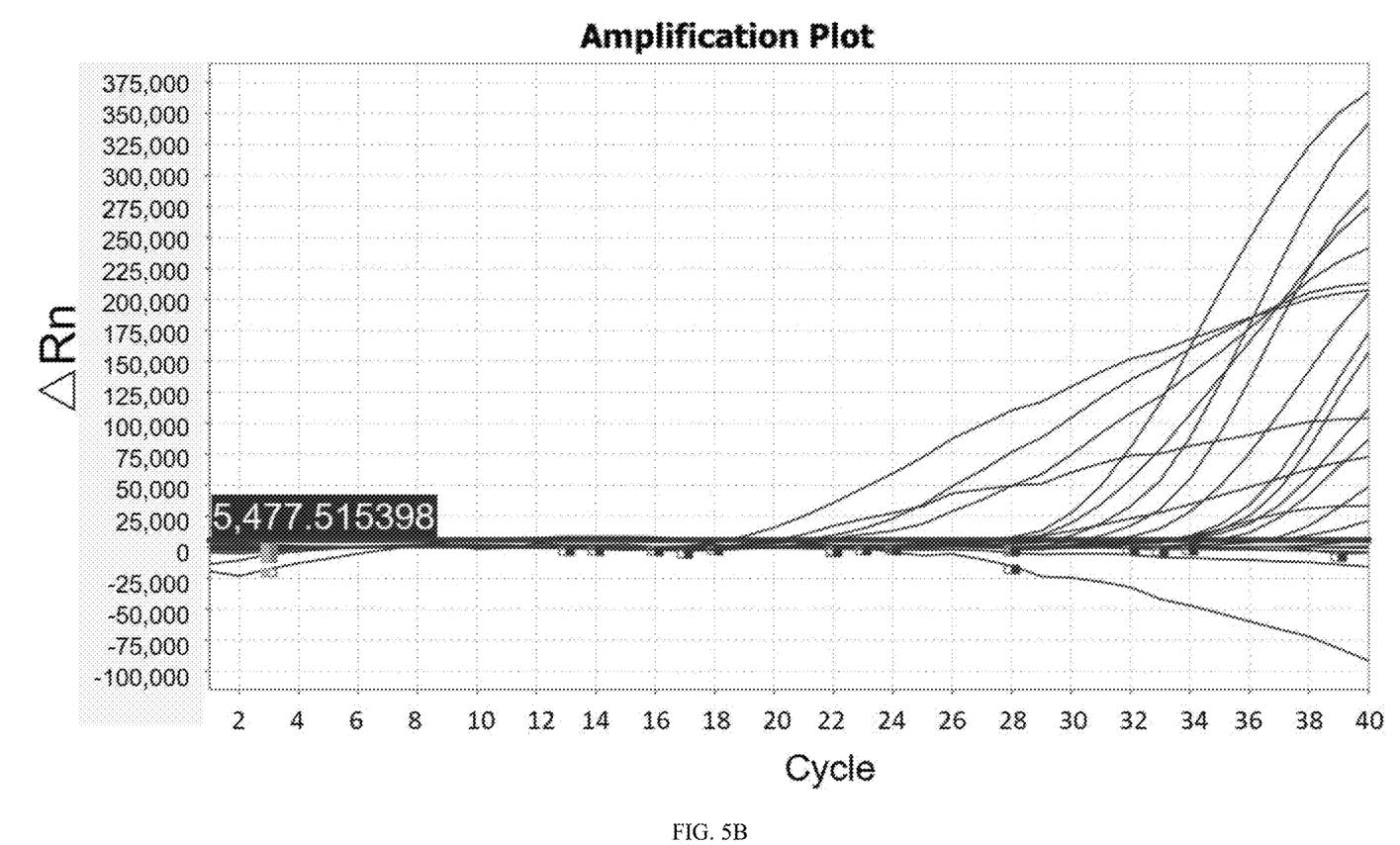

106 cell samples were detected by the commercial qPCR kit. Results showed that 41 cell samples had a CT value of smaller than 40 (Table 10) and a typical amplification curve, and were positive for *mycoplasma*, as shown in FIGS. 5A-5B. Thus, a positive detection rate was 38.68%.

TABLE 10

CT values of 106 cell samples detected
by the commercial qPCR kit

| No. | CT |
| --- | --- |
| 1 | Undet |
| 2 | 37.423 |
| 3 | Undet |
| 4 | Undet |
| 5 | 30.938 |
| 6 | Undet |
| 7 | 11.151 |
| 8 | Undet |
| 9 | 32.281 |
| 10 | Undet |
| 11 | 28.043 |
| 12 | Undet |
| 13 | 23.739 |
| 14 | Undet |
| 15 | Undet |
| 16 | 14.656 |
| 17 | Undet |
| 18 | Undet |
| 19 | 27.768 |
| 20 | Undet |
| 21 | Undet |
| 22 | 38.322 |
| 23 | 36.643 |
| 24 | Undet |
| 25 | 37.423 |
| 26 | Undet |
| 27 | Undet |
| 28 | 30.938 |
| 29 | 33.146 |
| 30 | Undet |
| 31 | Undet |
| 32 | 32.281 |
| 33 | Undet |
| 34 | 28.043 |
| 35 | Undet |
| 36 | 23.739 |
| 37 | 31.751 |
| 38 | Undet |
| 39 | Undet |
| 40 | Undet |
| 41 | 25.991 |
| 42 | 23.770 |
| 43 | Undet |
| 44 | 11.607 |
| 45 | Undet |
| 46 | Undet |
| 47 | 27.221 |
| 48 | Undet |
| 49 | 11.800 |
| 50 | Undet |
| 51 | Undet |
| 52 | Undet |
| 53 | Undet |
| 54 | Undet |
| 55 | 22.229 |
| 56 | Undet |
| 57 | 13.693 |
| 58 | Undet |
| 59 | 35.904 |
| 60 | Undet |
| 61 | Undet |
| 62 | Undet |
| 63 | Undet |
| 64 | 35.029 |
| 65 | Undet |
| 66 | 33.146 |
| 67 | Undet |
| 68 | Undet |
| 69 | Undet |
| 70 | 30.731 |
| 71 | Undet |
| 72 | Undet |
| 73 | Undet |
| 74 | Undet |
| 75 | Undet |
| 76 | 29.715 |
| 77 | 22.427 |
| 78 | Undet |
| 79 | 22.270 |
| 80 | 17.900 |
| 81 | Undet |
| 82 | Undet |
| 83 | 20.428 |
| 84 | Undet |
| 85 | Undet |
| 86 | 35.029 |

TABLE 10-continued

CT values of 106 cell samples detected by the commercial qPCR kit

| No. | CT |
| --- | --- |
| 87 | Undet |
| 88 | Undet |
| 89 | Undet |
| 90 | Undet |
| 91 | 31.751 |
| 92 | Undet |
| 93 | Undet |
| 94 | Undet |
| 95 | Undet |
| 96 | 30.731 |
| 97 | Undet |
| 98 | 31.068 |
| 99 | Undet |
| 100 | Undet |
| 101 | Undet |
| 102 | 16.515 |
| 103 | 29.855 |
| 104 | Undet |
| 105 | 13.274 |
| 106 | 27.545 |
| Pos | 11.27 |
| Neg | Undet |

4. Comparison of the Three Methods

The qPCR method in Example 1 completed the detection within 1 h, the commercial qPCR kit completed the detection in about 3 h, and the isolation and cultivation method took 21 d to 29 d to complete the detection of all cell samples.

TABLE 11

Comparison of detection performance of different methods

| Method | Time consumption | Detection rate | Coincidence rate with the gold standard (isolation and cultivation method) |
| --- | --- | --- | --- |
| qPCR in Example 1 | 1 h | 46.23% | 100% |
| Isolation and cultivation method | 21-29 d | 29.25% | 100% |
| Commercial qPCR | 3 h | 38.68% | 87.10% |

The collected 106 random cell samples were detected for *mycoplasma*, and results were shown in Table 11. 49 samples were detected as positive for *mycoplasma* contamination by the qPCR method in Example 1, which had a coincidence rate of 100% with the detection results of the classical cultivation method (a number of cell samples detected as positive by both methods/a number of cell samples detected as positive by the classical cultivation method * 100%). 41 samples were detected as positive by the commercial qPCR kit, and 4 samples were missed compared with the classical cultivation method. A coincidence rate of the commercial qPCR kit with the cultivation method was only 87.10%.

Therefore, when used in the detection of *mycoplasma*, the qPCR method in Example 1 is significantly superior to the prior art in terms of broad-spectrum activity, sensitivity, and accuracy.

```
A sequence of the gene fragment Spiroplasma (SEQ ID NO: 4) was
as follows:
AACATAACAACAAAAGATAATCATTTAATCAATGAATATCCGTCATTAAAGCTAGGAACAAA

AACGATATTTTTTAATGAGAGTTTGATCCTGGCTCAGGATGAACGCTGGCGGCATGCCTAAT

ACATGCAAGTCGAACGGGGTGCTTGCACCCAGTGGCGAACGGGTGAGTAACACGTATCTAA

TCTACCCATTAGCGGGGGATAACAGTTGGAAACGACTGATAATACCGCATACGACATTTTCT

GGCATCAGAGAATGTTAAAAGGTCCGTTTGGATCACTAATGGATGAGGATGCGGCGTATTAG

TTAGTTGGTGGGGTAATGGCCTACCAAGACAATGATACGTAGCCGAACTGAGAGGTTGATC

GGCCACATCGGGACTGAGACACGGCCCGAACTCCTACGGGAGGCAGCAGTAGGGAATTTT

TCACAATGGGCGAAAGCCTGATGGAGCAATGCCGCGTGACTGAAGACGGTCTTCGGATTGT

AAAAGTCTGTTGTAAGGGAAGAACAGTAAGTATAGGAAATGATACTTATTTGACGGTACCTT

ACCAGAAAGCCACGGCTAACTATGTGCCAGCAGCCGCGGTAATACATAGGTGGCAAGCGTT

ATCCGGATTTATTGGGCGTAAAGCGTGCGCAGACGGTTTAACAAGTTTGGGGTCAAATCCT

GGAGCTCAACTCCAGTTCGCCTTGAAAACTGTTAAGCTAGAGTGTAGGAAAGGTCGATGG

AATTCCATGTGTAGCGGTGAAATGCGTAGATATATGGAGGAACACCAGTGGCGAAGGCGGT

CGACTGGCCTATCACTGACGTTTAGGCACGAAAGCGTAGGGAGCAAATAGGATTAGATACC

CTAGTAGTCTACGCCGTAAACGATGAGTACTAAGTGTCGGACTAAGTTCGGTGCTGCAGCT

AACGCATTAAGTACTCCGCCTGAGTAGTATGCTCGCAAGAGTGAAACTCAAAGGAATTGAC

GGGGACCCGCACAAGCGGTGGAGCATGTGGTTTAATTCGAAGCAACGCGAAGAACCTTAC

CAAGGCTTGACATCCAGTGCAAAGCTGTAGAAATACAGTGGAGGTTAACATTGAGACAGGT

GGTGCATGGTTGTCGTCAGCTCGTGCCGTGAGGTGTTTGGTTAAGTCCAGTAACGAGCGCA

ACCCTTGCCGTTAGTTACTCCATTAAGTTGAGATACTCTAACAGGACTGCTAGTGTAAGCTA
```

-continued

```
GAGGAAGGTGGGGATGACGTCAAATCAGCATGCCCCTTATATCTTGGGCTACACACGTGCT

ACAATGGTCGGTACAAACAGTTGCGATCTCGTAAGAGGGAGCTAATCTGAAAAAGCCGATC

TCAGTTCGGATTGAGGGCTGCAACTCGCCCTCATGAAGCCGGAATCGCTAGTAATCGCGAA

TCAGCAATGTCGCGGTAATACGTTCTCGGGTCTTGTACACACCGCCCGTCACACCATGAG

AGTTGATAATACCAGAAGTCGGTATTCTAACCGCAAGGAGGAAGCCGCCCAAGGTAGGATT

GATGATTAGGGTGAAGTCGTAACAAGGTATCCGTACGAGAACGTGCGGATGGATCACCTCC

TTTCTATGGAGTTAATACTTTATAGTAATTAACTAGTTTTAATGACCGTTATGTTTAGTTTTCA

GAGATTAGTTTCTCTGAAAATAACAAGTAAATGTTATTGGAATTGTTCTTTGAAAACTGGAT

AATAGACATCTAGTTATTTTAATCACATGATTAAAATAACAATAATTCAAAATTTCTGTTATTT

TTAAAAAATAACTAAAATTTCACAGTTATATTTGTAAATGATTCTCAAAAAACTGATTTAAAA

TCAGGTCAAATAATTTATAAAACTTTGAAGTTACAAAGGGCGTATGGTGAATGCCTTGG.
```

---

What is claimed is:

1. A composition for detecting mycoplasma, wherein the composition is an aqueous solution comprising a primer M-F consisting of SEQ ID NO: 1;

a primer M-R consisting of SEQ ID NO: 2; and a probe M-P consisting of SEQ ID NO: 3, wherein the probe M-P further comprises a fluorophore carboxyfluorescein (FAM) linked at a 5' terminus and a quencher black hole quencher 1 (BHQ1) linked at a 3' terminus.

2. The composition according to claim 1, wherein the primer M-F, the primer M-R, and the probe M-P are in a molar concentration ratio of 1:(0.8-1.2):(0.8-1.2).

3. A kit for detecting mycoplasma, comprising the composition according to claim 1.

4. The kit according to claim 3, wherein the primer M-F, the primer M-R, and the probe M-P in the kit are in a molar concentration ratio of 1:(0.8-1.2):(0.8-1.2).

5. The kit according to claim 4, wherein the kit further comprises a positive plasmid, and the positive plasmid is obtained by inserting a fragment consisting of SEQ ID NO: 4 into a pUC57 plasmid vector.

6. A method for detecting mycoplasma using the composition according to claim 1 for a non-diagnostic purpose, comprising the following steps:

(1) extracting DNA from a sample;

(2) with the DNA of the sample as a template, conducting a quantitative polymerase chain reaction (qPCR) detection using the primer M-F, the primer M-R, and the probe M-P; and (3) when a cycle threshold (Ct) value of the qPCR detection for the DNA of the sample is smaller than 38 and there is a typical S-type amplification curve, determining the sample as positive, indicating that there is the mycoplasma in the sample; and when the Ct value of the qPCR detection for the DNA of the sample is larger than or equal to 38 or there is no Ct value or there is no typical S-type amplification curve, determining the sample as negative, indicating that there is no mycoplasma in the sample.

7. The method according to claim 6, wherein a reaction system for the qPCR detection comprises: 12.5 μL of a fluorescent polymerase chain reaction (PCR) solution, 1 μL of the DNA of the sample, 3 μL of the composition, and 8.5 μL of double distilled water (ddH$_2$O).

8. The method according to claim 7, wherein a procedure for the qPCR detection is as follows: 95° C. for 3 min; 95° C. for 15 sec, and 60° C. for 30 sec, with 40 amplification cycles in total.

9. The method according to claim 6, wherein the sample is a biological product.

10. The method according to claim 9, wherein the biological product is a cell, a serum, or a vaccine.

* * * * *

SEQUENCE LISTING

```
Sequence total quantity: 7
SEQ ID NO: 1          moltype = DNA   length = 20
FEATURE               Location/Qualifiers
source                1..20
                      mol_type = other DNA
                      organism = synthetic construct
SEQUENCE: 1
atccatcccc acgttctcgt                                              20

SEQ ID NO: 2          moltype = DNA   length = 21
FEATURE               Location/Qualifiers
source                1..21
                      mol_type = other DNA
                      organism = synthetic construct
SEQUENCE: 2
tgcggtgaat acgttctcgg g                                            21

SEQ ID NO: 3          moltype = DNA   length = 16
FEATURE               Location/Qualifiers
source                1..16
                      mol_type = other DNA
                      organism = synthetic construct
SEQUENCE: 3
acgggcggtg tgtaca                                                  16

SEQ ID NO: 4          moltype = DNA   length = 1901
FEATURE               Location/Qualifiers
source                1..1901
                      mol_type = genomic DNA
                      organism = Spiroplasma sp.
SEQUENCE: 4
aacataacaa caaagataa  tcatttaatc aatgaatatc cgtcattaaa gctaggaaca    60
aaaacgatat tttttaatga gagtttgatc ctggctcagg atgaacgctg gcggcatgcc   120
taatacatgc aagtcgaacg gggtgcttgc acccagtggc gaacgggtga gtaacacgta   180
tctaatctac ccattagcgg gggataacag ttggaaacga ctgataatac cgcatacgac   240
attttctggc atcagagaat gttaaaaggt ccgtttggat cactaatgga tgaggatgcg   300
gcgtattagt tagttggtgg ggtaatggcc taccaagaca atgatacgta gccgaactga   360
gaggttgatc ggccacatcg ggactgagac acggcccgaa ctcctacggg aggcagcagt   420
agggaatttt tcacaatggg cgaaagcctg atggagcaat gccgcgtgac tgaagacggt   480
cttcggattg taaagtctgt tgtaaggga  agaacagtaa gtataggtaa tgatacttat   540
ttgacggtac cttaccagaa agccacggct aactatgtgc cagcagccgc ggtaatacat   600
aggtggcaag cgttatccgg atttattggg cgtaaagcgt gcgcagacgg tttaacaagt   660
ttggggtcaa atcctggagc tcaactccag ttcgccttga aaactgttaa gctagagtgt   720
aggaaaggtc gatggaattc catgtgtagc ggtgaaatgc gtagatatat ggaggaacac   780
cagtggcgaa ggcggtcgac tggcctatca ctgacgttta ggcacgaaag cgtagggagc   840
aaataggatt agataccccta gtagtctacg ccgtaaacga tgagtactaa gtgtcggact   900
aagttcggtc ctgcagctaa cgcattaagt actccgcctg agtagtatgc tcgcaagagt   960
gaaactcaaa ggaattgacg gggacccgca caagcggtgg agcatgtggt ttaattcgaa  1020
gcaacgcgaa gaaccttacc aaggcttgac atccagtgca aagctgtaga aatacagtgt  1080
aggttaacat tgagacaggt ggtgcatggt tgtcgtcagc tcgtgccgtg aggtgtttgg  1140
ttaagtccga taacgagcgc aacccttgcc gttagttact ccattaagtt gagatactct  1200
aacaggactg ctagtgtaag ctagaggaag gtggggatga cgtcaaatca gcatgccct   1260
```

```
tatatcttgg gctacacacg tgctacaatg gtcggtacaa acagttgcga tctcgtaaga      1320
gggagctaat ctgaaaaagc cgatctcagt tcggattgag ggctgcaact cgccctcatg      1380
aagccggaat cgctagtaat cgcgaatcag caatgtcgcg gtgaatacgt tctcgggtct      1440
tgtacacacc gcccgtcaca ccatgagagt tgataatacc agaagtcggt attctaaccg      1500
caaggaggaa gccgcccaag gtaggattga tgattagggt gaagtcgtaa caaggtatcc      1560
gtacgagaac gtgcggatgg atcacctcct ttctatggag ttaatactt  atagtaatta      1620
actagtttta atgaccgtta tgtttagttt tcagagatta gtttctctga aaataacaag      1680
taaatgttat tggaattgtt ctttgaaaac tggataatag acatctagtt attttaatca      1740
catgattaaa ataacaataa ttcaaaattt ctgttatttt taaaaaataa ctaaaatttc      1800
acagttatat ttgtaaatga ttctcaaaaa actgatttaa aatcaggtca aataatttat      1860
aaaactttga agttacaaag ggcgtatggt gaatgccttg g                          1901

SEQ ID NO: 5               moltype = DNA  length = 22
FEATURE                    Location/Qualifiers
source                     1..22
                           mol_type = other DNA
                           organism = synthetic construct
SEQUENCE: 5
ggtcgtctac gtcaaaactt gc                                                22

SEQ ID NO: 6               moltype = DNA  length = 21
FEATURE                    Location/Qualifiers
source                     1..21
                           mol_type = other DNA
                           organism = synthetic construct
SEQUENCE: 6
gccatttggt ccccgtcaaa g                                                 21

SEQ ID NO: 7               moltype = DNA  length = 16
FEATURE                    Location/Qualifiers
source                     1..16
                           mol_type = other DNA
                           organism = synthetic construct
SEQUENCE: 7
taccttgtta cgactt                                                       16
```